US010900085B2

(12) United States Patent
Solmi et al.

(10) Patent No.: US 10,900,085 B2
(45) Date of Patent: Jan. 26, 2021

(54) METHOD AND KIT FOR THE DIAGNOSIS OF COLORECTAL CANCER

(71) Applicant: ALMA MATER STUDIORUM—UNIVERSITÀ DI BOLOGNA, Bologna (IT)

(72) Inventors: Rossella Solmi, Bologna (IT); Gabriella Mattei, Bologna (IT); Giampaolo Ugolini, Bologna (IT); Maria Rodia, Bologna (IT); Mattia Lauriola, Bologna (IT); Isacco Montroni, Bologna (IT)

(73) Assignee: Alma Mater Studiorum—Università di Bologna, Bologna (IT)

( * ) Notice: Subject to any disclaimer, the term of this patent is extended or adjusted under 35 U.S.C. 154(b) by 120 days.

(21) Appl. No.: 15/576,225

(22) PCT Filed: May 23, 2016

(86) PCT No.: PCT/IB2016/052999
§ 371 (c)(1),
(2) Date: Nov. 21, 2017

(87) PCT Pub. No.: WO2016/185451
PCT Pub. Date: Nov. 24, 2016

(65) Prior Publication Data
US 2019/0024180 A1 Jan. 24, 2019

(30) Foreign Application Priority Data
May 21, 2015 (IT) .......................... 102015000016638

(51) Int. Cl.
*C12Q 1/6886* (2018.01)
(52) U.S. Cl.
CPC ..... *C12Q 1/6886* (2013.01); *C12Q 2600/158* (2013.01); *G01N 2333/4724* (2013.01); *G01N 2333/705* (2013.01); *G01N 2333/70503* (2013.01); *G01N 2333/78* (2013.01)

(58) Field of Classification Search
None
See application file for complete search history.

(56) References Cited

U.S. PATENT DOCUMENTS

2005/0191634 A1 9/2005 Lin et al.

FOREIGN PATENT DOCUMENTS

| WO | 01/73027 | 10/2001 |
| WO | 2010/118166 | 10/2010 |

OTHER PUBLICATIONS

Blumenthal et al., "Expression patterns of CEACAM5 and CEACAM6 in primary and metastatic cancers," BMC Cancer, vol. 7, No. 2, pp. 1-15. (Year: 2007).*
Kim et al., "Overexpression and clinical significance of carcinoembryonic antigen-related cell adhesion molecule 6 in colorectal cancer," Clinica Chimica ACTA, vol. 415, pp. 12-19. (Year: 2013).*
Rodia et al., "Systematic large-scale meta-analysis identifies a panel of two mRNAs as blood biomarkers for colorectal cancer detection," Oncotarget, vol. 7, No. 21, pp. 30295-30306. (Year: 2016).*
Okuda et al., "Frequent Deletion of p16INK4a/MTS1 and p15INK4b/MTS2 in Pediatric Acute Lymphoblastic Leukemia," Blood, vol. 85, No. 9, pp. 2321-2330. (Year: 1995).*
Wacholder et al., "Assessing the Probability That a Positive Report is False: An Approach for Molecular Epidemiology Studies," Journal of the National Cancer Institute, vol. 96, No. 6, pp. 434-442. (Year: 2004).*
Ioannidis et al., "Replication validity of genetic association studies," Nature Genetics, vol. 29, pp. 306-309. (Year: 2001).*
Lucentini, J., "Gene Association Studies Typically Wrong," The Scientist, vol. 18, No. 24, pp. 1-4 (print out) (Year: 2004).*
International Search Report for PCT/IB2016/052999, five pages (dated Aug. 2016).
Written Opinion of the ISA for PCT/IB2015/052999, six pages (dated Aug. 2016).
Lauriola et al. "Identification by a Digital Gene Expression Displayer (DGED) and test by RT-PCR analysis of new mRNA candidate markers for colorectal cancer in peripheral blood" *International Journal of Oncology*, vol. 37, No. 2, pp. 519-525 (Aug. 2010).
García-García & Santos-Rodríguez "Spectral clustering and feature selection for microarray data" *2009 International Conference on Machine Learning and Applications*, pp. 425-428 (Dec. 2009).

* cited by examiner

*Primary Examiner* — Young J Kim
(74) *Attorney, Agent, or Firm* — Sterne, Kessler, Goldstein & Fox P.L.L.C.

(57) ABSTRACT

The present invention relates to a method for the diagnosis of colorectal cancer from a sample of blood or blood fractions, and to a kit for said diagnosis.

7 Claims, 2 Drawing Sheets

Figure 1:
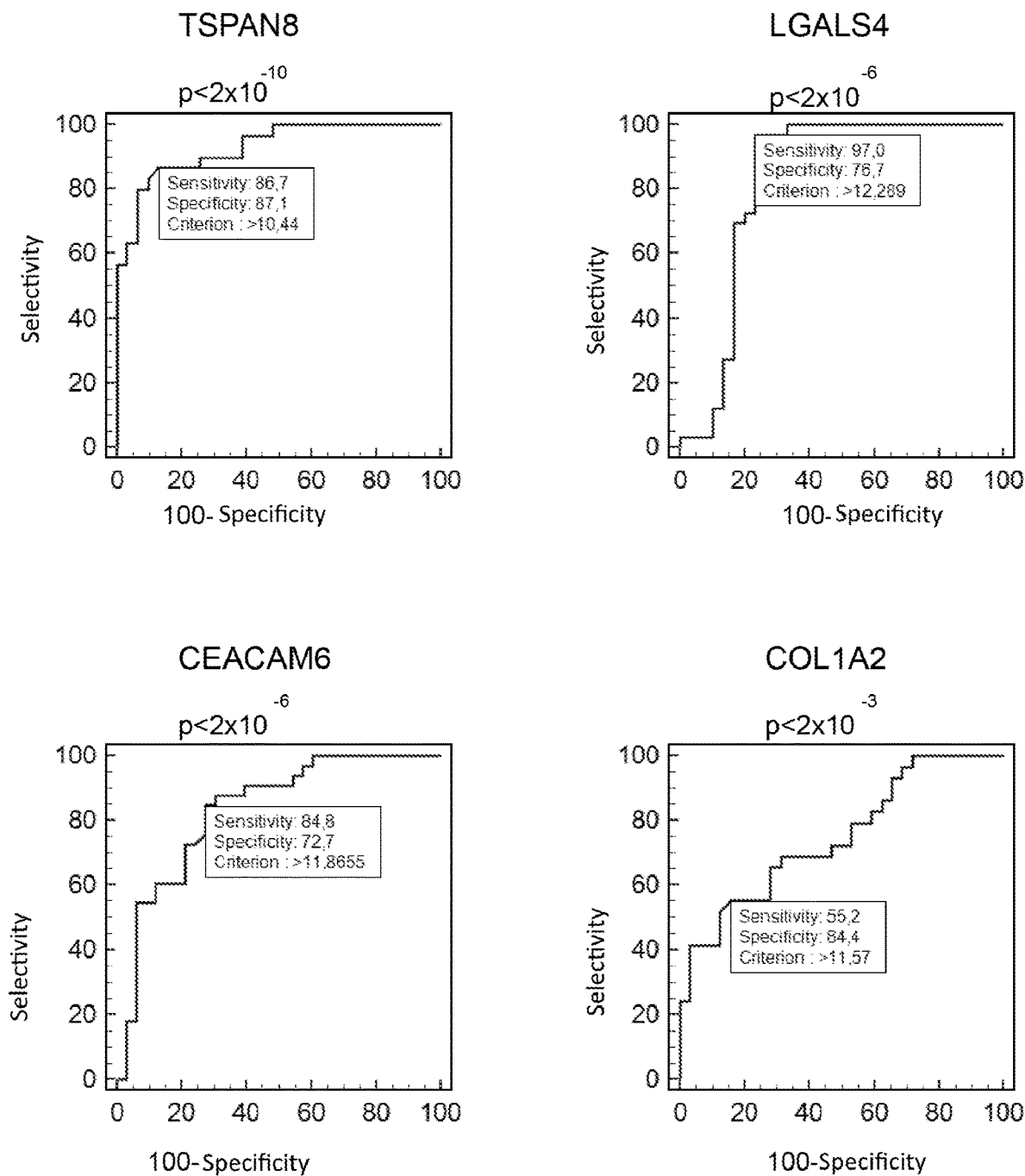

Specification includes a Sequence Listing.

METHOD AND KIT FOR THE DIAGNOSIS OF COLORECTAL CANCER

This application is the U.S. national phase of International Application No. PCT/IB2016/052999, filed May 23, 2016, which designated the U.S. and claims priority to Application No. IT 102015000016638, filed May 21, 2015; the entire contents of each of which are hereby incorporated by reference.

DESCRIPTION

The present invention relates to a method for the diagnosis of colorectal cancer from a sample of blood or blood fractions and a kit for said diagnosis.

PRIOR ART

Colorectal cancer (CRC) is the third most common cancer worldwide, with almost 1.4 million new cases diagnosed in 2012. A significant survival rate is obtained if the primary tumor is detected at an early stage.

In most CRC cases a multi-stage process develops, starting with benign precancerous adenomas that develop into aggressive metastatic carcinoma. This makes early diagnosis fundamental in order to benefit from the chances of a positive outcome for CRC patients.

Various noninvasive screening modes have been studied, including stool (fecal) tests detecting the presence of hemoglobin or blood in feces, and improved stool tests which also envisage integral DNA extraction. Very recently, a multi-target stool DNA examination has been proposed, Cologuard (Exact Sciences Corporation, Madison Wis.), approved by the Food and Drug Administration (FDA); yet, given the high rate of false positives in stool DNAs, further adjustments are needed. Moreover, in 2010, the CellSearchVR system (Veridex, Johnson-Johnson, USA) for the enumeration of circulating tumor cells (CTCs) in metastatic colorectal cancer (mCRC), based on immunofluorescence detection, has received FDA approval. Recently, a combinatory panel of seven mRNA biomarkers in blood: annexin A3 (ANXA3), C-Type lectin domain family 4, member D (CLEC4D), Lamin B1 (LMNB1), Proline Rich (transmembrane) 4-rich Gla (G-carboxyglutamic acid) 4 (transmembrane) (PRRG4), Tumor Necrosis Factor alpha-induced protein 6 (TNFAIP6), Vanin 1 (VNN1), and Interleukin 2 receptor beta (IL2RB), has been proposed by Marshall et. (Marshall K W, Mohr S, Khettabi F E, Nossova N, Chao S, Bao W, et al. A blood-based biomarker panel for stratifying current risk for colorectal cancer. International journal of cancer Journal international du cancer. 2010; 126(5):1177-86) (ColonSentry®, Canada-. Enzo Biochem USA). The test was recently approved by the New York Health Department as a test for determining a person's risk of having CRC. The research of markers as a screening instrument in a patient's blood represents a research topic for colorectal cancer early diagnosis. Numerous reports include encoding mRNAs, microRNAs (miRNAs), proteins, metabolites, DNA mutations and methylation markers. To date, the main trends of research on candidate mRNA markers generally involve various types of experimental tests: circulating tumor cells (CTCs), cancer stem cells (CSCs) (17) and circulating free RNA. Metastatic diffusion occurs quite early in tumor development; therefore, a specific and sensitive detection of CTCs became crucial for diagnosis. Quantitative PCR (qPCR) has recently been described as a good method for CTC quantification.

cfRNAs might be excellent tumor biomarkers of blood, as they might be more informative and accurate with respect to protein biomarkers. Various research groups have studied the potential use of circulating mRNA as a marker for cancer. The general experimental strategy is to employ microarray technology to analyse mRNA expression profile, followed by a quantitative Real Time PCR (qRT-PCR). The samples used are mRNAs that can be extracted directly from the blood, serum/plasma or from isolated blood cells.

In the state of the art, the need of a simple and reliable test that may be carried out on whole blood and not requiring, therefore, stool (feces) manipulation or extraction procedure of CTCs or CSCs or blood fractions, is felt. Among other things, a reliable test that may be carried out on whole blood does not entail the risk of losing, in the various manipulation steps, CTCs and/or CSCs whose number is critical for assay success.

RNA analysis is based on the fact that tumor phenotype variations associate with changes in the mRNA levels of genes regulating or affecting these changes. This led to the use of qRT-PCR.

SUMMARY OF THE INVENTION

The present invention provides a method and a diagnostic kit for the early diagnosis of colorectal cancer. The Authors of the present invention have identified and analysed specific RNAs exhibiting the highest different expression ratios between blood samples from healthy individuals and from individuals affected by CRC, and have identified some candidate RNAs. Among these, they have identified a peculiar combination of RNAs that enables to obtain results with a >90% sensitivity and a >90% specificity, where the sensitivity of a test is proportional to the ability of said test to correctly identify diseased subjects, and the specificity is the ability of said test to correctly single out healthy individuals. As a technician in the field is well-aware of, sensitivity and specificity values are obtained from a graph (ROC curve) representing an area (AUC) whose best value is 1 (area of a perfect square, with ordinate and abscissa coinciding with value 100).

Climbing up from the area, and more precisely from the topmost, leftwise-projecting point (the area at issue is more or less "stepped" on the left side of the graph) the specificity percentage (on the abscissa) and the sensitivity percentage (on the ordinate) are determined. The more the area tends to a square with value 1, the highest are the specificity and sensitivity percentages. The two values hardly go in the same direction, for instance, high specificity (ability to correctly identify healthy subjects) values are often related to low sensitivity (ability to correctly identify diseased subjects) values.

In the field of CRC diagnosis, for instance, the Fecal Occult Blood Test (FOBT), though highly specific (being in fact able to identify even very small blood traces present in the feces), is not very sensitive, as it is unable to discriminate the cases in which bleeding occurs for reasons independent of a tumor presence, so much that only one third of FOBT-positive cases are found to be diseased in a subsequent colonoscopy inspection.

The Authors of the present invention instead provide a diagnostic method and kit having high sensitivity and high specificity.

Therefore, object of the present invention are: a method for the diagnosis of colorectal cancer from a sample of human whole blood and/or of blood fractions comprising nucleic acids, comprising the steps of a. extracting total RNA or mRNA from said sample b. carrying out a quantitative analysis of the human genes TSPAN8, LGALS4, CEACAM6, COL1A2 mRNAs, wherein an overexpression of TSPAN8 and COL1A2 and an underexpression of LGALS4 and CEACAM6 with respect to a healthy control sample indicate the presence of colorectal cancer; and a kit comprising one or more aliquots of reagents suitable for carrying out the above-indicated method.

The method of the present invention can be used also in association with a therapeutic method for monitoring disease progression, and for control screenings subsequent to a therapeutic treatment of colorectal cancer.

DETAILED DESCRIPTION OF THE FIGURES

FIG. 1 (panels a, b, c, d): ROC curves of the individual markers of the invention, TSPAN8, LGALS4, CEACAM6 and COL1A2.

To assess diagnostic accuracy in terms of specificity and sensitivity of the markers of the present invention, ROC analysis was carried out. The markers of the invention yielded, as area under the curve (AUC), the following values: TSPAN8 (0.93), LGALS4 (0.827), CEACAM6 (0.806) and COL1A2 (0.748).

Figure 2:
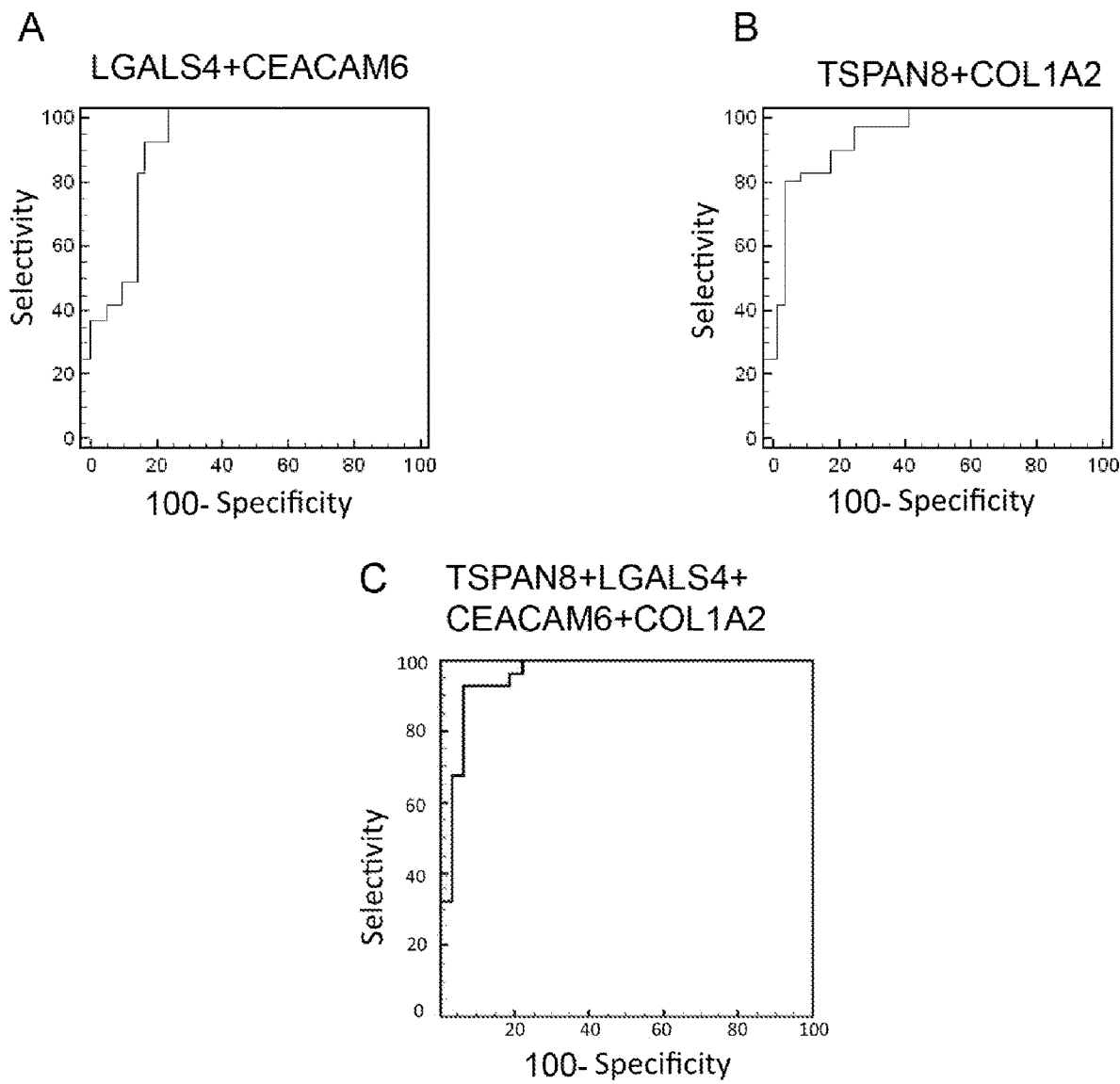

FIG. 2 (panels a, b, c): ROC curves for some combinations of the markers of the invention.

The figure shows how the combination of the four markers enables a specificity and a diagnostic selectivity higher than combinations of some of the markers of the invention with very high individual ROCs.

Panel A. LGALS4+CEACAM6; Panel B. TSPAN8+COL1A2;

Panel C. TSPAN8+LGALS4+CEACAM6+COL1A2. Full data are reported in Table 1.

DETAILED DESCRIPTION OF THE SEQUENCES

```
RT-PCR primer for TSPAN8
                                    SEQ ID NO: 1
gctgcatgcttctgttgtttt RT-PCR primer rev for TSPAN8
                                    SEQ ID NO: 2
aacacaattatggcttcctg RT-PCR primer for COL1A2
                                    SEQ ID NO: 3
gtggttactactggattgac RT-PCR primer rev for COL1A2
                                    SEQ ID NO: 4
ctgccagcattgatagtttc RT-PCR primer for LGALS4
                                    SEQ ID NO: 5
ttaccctggtcccggacatt RT-PCR primer rev for LGALS4
                                    SEQ ID NO: 6
agcctcccgaaatatggcac RT-PCR primer for CEACAM6
                                    SEQ ID NO: 7
cacagtctctggaagtgctcc RT-PCR primer rev for CEACAM6
                                    SEQ ID NO: 8
ggccagcactccaatcgt RT-PCR primer for B2M
                                    SEQ ID NO: 9
tgcctgccgtgtgaaccatgt RT-PCR primer rev for B2M
                                    SEQ ID NO: 10
tgcggcatcttcaaacctccatga RT-PCR primer for EPCAM
                                    SEQ ID NO: 11
gtatgagaaggctgagataaag RT-PCR primer REV for EPCAM
                                    SEQ ID NO: 12
cttcaaagatgtcttcgtcc RT-PCR primer for SPINK1
                                    SEQ ID NO: 13
tgaaaatcggaaacgccagac RT-PCR primer REV for SPINK1
                                    SEQ ID NO: 14
gcggtgacctgatgggattt RT-PCR primer for CDH1
                                    SEQ ID NO: 15
cagtacaacgacccaaccca RT-PCR primer REV for CDH1
                                    SEQ ID NO: 16
cacgctgacctctaaggtgg
```

DETAILED DESCRIPTION OF THE INVENTION

As discussed in the section related to the prior art, colorectal cancer is a disease with a very high incidence, for which it is necessary to have the availability of diagnostic screening methods that be reliable and easy to carry out.

For diagnostic purposes, the higher the sensitivity and the specificity, the more reliable the diagnosis.

The sensitivity and specificity values are obtained from a graph (ROC curve) representing an area (AUC) whose best value is 1 (area of a perfect square with ordinate and abscissa coinciding with value 100).

Climbing up from the area, and more precisely from the topmost, leftwise-projecting point (the area at issue is more or less "stepped" on the left side of the graph) the specificity percentage (on the abscissa) and the sensitivity percentage (on the ordinate) are determined. The more the area tends to a square with value 1, the higher are the specificity and sensitivity percentages.

However, as already discussed above, the sensitivity and specificity values hardly go in the same direction; often, in fact, high specificity (ability to correctly identify healthy subjects) values are related with low sensitivity (ability to correctly identify diseased subjects) values.

For instance, the Fecal Occult Blood Test (FOBT) commonly used for colorectal cancer diagnosis, though being highly specific (in fact, it is able to identify even very small blood traces present in the feces), is not very sensitive, as it does not enable to discriminate the cases in which bleeding occurs due to reasons independent from the presence of a tumor, so much that in a subsequent colonoscopy inspection only ⅓ of FOBT-positive cases are found to be diseased.

Evidently, therefore, a test with high specificity and sensitivity is needed in the present state of the art, since a test meeting these requirements has an economical value added (as it enables to proceed with a colonoscopy only on individuals actually having a very high probability of having a colorectal cancer), but, above all, an enormous psychological value, as it enables to rule out false positives with higher accuracy, avoiding the entailed psychological repercussions on the same individuals.

The Authors of the present invention have singled out, in a wide panel of putative markers, four markers whose combined analysis enables to reach sensitivity and specificity values of >90% for each parameter.

As to the markers identified by the Inventors, with the exception of marker TSPAN8, these markers exhibit, as is usually the case, a reverse correlation between sensitivity and specificity values; therefore, to high sensitivity values there correspond low specificity values, and vice versa, whereas the combined analysis of these four markers enables to sensibly improve the parameters, in terms of both specificity and sensitivity.

As demonstrated by the data summarized in Table 1 and discussed below, the progressive association of 2, 3, up to 4 markers, absolutely did not enable to foresee that the set of the 4 markers would have provided the selectivity and specificity values obtained.

In fact, the data reported in the table show how it is entirely impossible to foresee the result, in terms of sensitivity and specificity of the combined analysis, analysing in parallel the various combinations of the four markers selected by the Inventors.

The present invention therefore provides a method for the diagnosis of colorectal cancer from a sample of human whole blood or blood fractions comprising nucleic acids, comprising the steps of
a. extracting total RNA or mRNA from said sample
b. carrying out a quantitative analysis of the human genes TSPAN8, LGALS4, CEACAM6, COL1A2 mRNAs, wherein
an overexpression of TSPAN8 and COL1A2 and underexpression of LGALS4 and CEACAM6 indicate the presence of colorectal cancer.

According to the invention, the human gene TSPAN8 is Tetraspanin 8 gene, whose RNA has RNA Genbank accession number NM_004616.

According to the invention, the human gene COL1A2 is Collagen, type I, alpha 2 gene, whose RNA has RNA Genbank accession number NM_000089.

According to the invention, the human gene LGALS4 is Lectin, galactoside-binding, soluble, 4 gene, whose RNA has RNA Genbank accession number NM_006149.

According to the invention the human gene CEACAM6 is Carcinoembryonic antigen-related adhesion molecule 6 gene, whose RNA has RNA Genbank accession number NM_002483. According to the invention, the sample of the method of the present invention may be a sample of whole blood or of any one blood fraction comprising nucleic acids, like, e.g., serum and/or plasma.

For the purposes of the present invention, by overexpression it is meant an expression higher than the physiological one, that may be assessed by comparing the expression values for each gene analysed with respect to those present in control healthy individuals or with respect to a preassigned (predetermined) cutoff.

By underexpression, for the purposes of the present invention, it is meant an expression lower than the physiological one, that may be assessed by comparing the expression values for each gene analysed with respect to those present in control healthy individuals or with respect to a preassigned (predetermined) cutoff.

By physiological expression it is meant that normally detected in healthy individuals.

According to one embodiment of the present invention, therefore, the expression values for each of the genes analysed may be obtained by quantifying the mRNA for each gene in the sample of interest, and comparing said values either with respect to those obtained in control healthy samples, or with respect to a cutoff calculated in advance for each gene.

In the method according to the invention, therefore, said overexpression and underexpression of said reference values can be obtained from a control sample collected from a healthy individual (or from a pool of control samples collected from healthy individuals) or with respect to a cutoff predetermined for each RNA of interest.

The control sample collected from a healthy individual could be a sample of total mRNA or RNA, or even be a mRNA or cDNA pool comprising, respectively, mRNAs or cDNAs of interest obtained from healthy individuals. Alternatively, when the expression is quantified with respect to a cutoff predetermined for each RNA, this cutoff will be a cutoff that has been determined in advance, for each of the RNAs of interest, from a sample of blood or blood fractions collected from healthy individuals.

For the purposes of the present invention, the quantitative analysis of the mRNAs may be carried out by using any one method of quantitative mRNA analysis known to a technician in the field, like, e.g. real-time quantitative PCR, or digital PCR or ultra deep-sequencing.

In a preferred embodiment, the quantitative analysis at b. is carried out by Real Time PCR, which is a technique well-known to a person skilled in the art.

Real-time PCR, also referred to as quantitative PCR or real-time quantitative PCR (rtq-PCR), is a method of simultaneous DNA amplification (polymerase chain reaction, or PCR) and quantification.

As known to a technician in the field, RNA or mRNA extraction enables to create cDNA by reverse-transcription PCR, which may be amplified by DNA-polymerase chain reaction and quantified after each amplification cycle. Common quantification methods include the use of fluorescent dyes that intercalate with the double-strand (ds) DNA and modified DNA oligonucleotides (referred to as probes) that fluoresce when hybridized with a DNA. Therefore, by Real-Time PCR it is possible to measure the relative expression of a gene at a specific time, either in a cell or in a specific tissue type. The combination of these two techniques is often referred to as quantitative RT-PCR.

As known to a technician in the field, by Real Time PCR an absolute quantification of the concentration of specific RNAs can be carried out by producing a standard calibration curve, or, alternatively, a relative quantification can be carried out by comparing their amount to that of a control gene.

Absolute quantification can use standard samples (plasmid DNA or other DNA forms) whose absolute concentration is known. It must be certain, however, that PCR efficiency be the same for known samples and unknown ones. The relative quantification method is simpler, as it requires the quantification of human control or housekeeping genes to normalize the expression of the studied gene.

The primers for real-time PCR can be easily designed by the technician in the field by suitable programs available to the public, even on the Internet, since the sequences of the markers of the present invention are available on the RNA Genbank and the accession numbers for each marker are provided in the present description.

By way of a mere example, in no way binding for the implementation of the present invention, herein primer pairs for Real Time PCR are provided, suitable for the implementation of the method described herein.

The primer pairs may be designed so as to be used in a single reaction, as they function under the same PCR conditions and do not form aspecific amplificates.

Primer pairs for Real Time PCR specific for sequences of interest are commercially available (e.g., Sigma Aldrich).

According to an exemplary and non-limiting embodiment of the present invention, Real Time PCR can be carried out by using the primers of SEQ ID NOS: 1 and 2 for TSPAN8; the primers of SEQ ID NOS: 3 and 4 for COL1A2, the primers of SEQ ID NOS: 5 and 6 for LGALS4 and the primers of SEQ ID NOS: 7 and 8 for CEACAM6.

Evidently, the sequences of the mRNAs to be quantified being known, the technician in the field could easily design other suitable primer pairs that may be used in a single Real Time PCR reaction and which do not produce aspecific amplificates.

The primer pairs will have the chemical modifications commonly used for Real Time PCR primers.

In a preferred embodiment, the method of the present invention also provides the amplification and the quantification, by the same Real Time PCR, of one or more human control housekeeping genes for the normalization of the values obtained for the markers of interest. For instance, the human gene B2M, of beta 2 microglobulin, whose RNA Genbank accession number is NM_004048, can be used as control gene.

A non-limiting example of primer for the quantification of a control gene is given by the primers of SEQ ID NOS: 9 and 10, which enable gene B2M quantification. Evidently, a person skilled in the art could easily design other primers for the quantification of B2M, or of any other constitutively expressed human gene to be used as control.

For the purposes of the present invention, the term primer has the meaning commonly used in the literature, therefore indicating an oligonucleotide of a length normally ranging from 9 to 50 nucleotides, normally from 15 to 30 nucleotides, with a sequence enabling it to specifically and efficiently hybridize to the sequence of interest, neglecting the aspecific ones.

Evidently, in the method of the present invention, any mRNA of human housekeeping gene to be used as control for the normalization of the values obtained for the mRNAs of the genes TSPAN8, LGALS4, CEACAM6, COL1A2 could be amplified.

As already mentioned, normalization could be carried out with respect to one or more control genes.

Therefore, the normalization will enable to calculate a normalized Ct value, denoted in the present description as $\Delta Ct$, having calculated for each sample analysed the CT of each marker of interest (TSPAN8, LGALS4, CEACAM6, COL1A2), normalizing it with respect to the CT of a constitutively expressed (housekeeping) gene with the following operation:

$$\Delta Ct_{marker\ of\ interest} = CT_{marker\ of\ interest} - CT_{constitutive\ gene}$$

therefore, by way of example, $$\Delta Ct_{TSPAN8} = CT_{TSPAN8} - CT_{B2M}$$

In one embodiment of the present invention, therefore, the quantitative analysis of the method comprises the assessment of the Ct for each marker and the assessment of the normalized $\Delta Ct$ with respect to a constitutively expressed gene for each marker.

In this embodiment, the individuals affected by colorectal cancer have a $\Delta Ct$ of $\leq 11.9 \pm 1.7$ for TSPAN8; a $\Delta Ct$ of $\leq 11.8 \pm 2.28$ for COL1A2; a $\Delta Ct$ of $\geq 11.42 \pm 2.42$ for LGALS4, and a $\Delta Ct$ of $\geq 10.9 \pm 1.79$ for CEACAM6. As anticipated above, the invention provides a method with specificity and selectivity values higher than 90% for each parameter.

Table 1 reports below the values observed for various markers and for all the combinations of the 4 markers selected herein.

Evidently, none of the combinations assayed, with the exception of that comprising the 4 markers selected, exhibits both parameters, of selectivity and specificity, higher than 90%. Moreover, none of the data on the 2- or 3-marker combinations could have allowed to presume the effect observed with all 4.

TABLE 1

| Marker/s | Number (n) of CRC patients | AUC | Sensitivity % | Specificity % |
|---|---|---|---|---|
| TSPAN8 | 32 | 0.930 | 86.7 | 87.1 |
| EPCAM | 27 | 0.631 | — | — |
| SPINK 1 | 35 | 0.503 | — | — |
| COL1A2 | 32 | 0.748 | 55.1 | 84.4 |
| CDH1 | 28 | 0.581 | — | — |
| LGALS4 | 33 | 0.827 | 97 | 76.7 |
| CEACAM6 | 33 | 0.806 | 84.8 | 70.4 |
| COL1A2 + LGALS4 | 32 | 0.820 | 90 | 75 |
| COL1A2 + CEACAM6 | 32 | 0.870 | 87 | 77 |
| LGALS4 + CEACAM6 | 33 | 0.914 | 92.5 | 85 |
| TSPAN8 + COL1A2 | 33 | 0.901 | 82 | 95 |
| TSPAN8 + LGALS4 | 32 | 0.89 | 90 | 80 |
| TSPAN8 + CEACAM6 | 32 | 0.92 | 80 | 92 |
| TSPAN8 + LGALS4 + COL1A2 + CEACAM6 | 32 | 0.959 | 92.5 | 94 |
| TSPAN8 + LGALS4 + CEACAM6 | 32 | 0.93 | 92 | 82 |
| TSPAN8 + LGALS4 + COL1A2 | 32 | 0.89 | 75 | 65 |
| TSPAN8 + COL1A2 + CEACAM6 | 32 | 0.90 | 82 | 93 |
| LGALS4 + COL1A2 + CEACAM6 | 32 | 0.87 | 80 | 78 |

As can be seen in the Table above, the only case in which both sensitivity and specificity unexpectedly exceed 90% values is had when the 4 markers TSPAN8, LGALS4, CEACAM6, COL1A2 are analysed.

The AUC column represents diagnostic accuracy expressed in terms of "area under the curve" of the various combinations and of the individual markers; evidently, only the combination of the 4 markers is able to yield a >0.95 diagnostic accuracy.

The present invention therefore provides a diagnostic method, in any of the embodiments described above, with a >90% specificity and a >90% sensitivity; more particularly, a diagnostic method with a sensitivity of about 92.5% and a specificity of about 94%, i.e. a diagnostic method with a sensitivity higher than that of colonoscopy and of the FOBT test, and a specificity approaching that of colonoscopy, and which however is higher than that of the FOBT test.

As to the fecal occult blood test (FOBT), generally, the sensitivity of a single FOBT test is deemed to range from 10 to 40%, and only by carrying out 3 sample collections for 3 consecutive days the sensitivity might be brought even to 92%, whereas the specificity is anyhow of 90%. FOBT-positive patients subsequently undergo a more in-depth examination, which is colonoscopy, with a 90% sensitivity and 100% specificity. Only one-third of FOBT-positive patients prove to be ill with colorectal carcinoma, and the diagnosis is made by colonoscopy. The method of the present invention provides the possibility of carrying out a test requiring only one collection and exhibiting a 92.5% sensitivity and a 94% specificity. This means that, due to its high reliability, it could replace the current stool test, but also and above all colonoscopy, which is an invasive and particularly costly test.

The method provided herein can be used as a simple diagnostic or screening method for patient populations, but can also be used to monitor the progress of a therapy against colorectal cancer, or for a post-therapeutic monitoring of individuals that have undergone systemic and/or surgical therapy against said cancer.

Evidently, in fact, since the method of the invention enables a high-specificity, high-selectivity diagnosis of colorectal cancer, and since said analysis does not envisage invasive interventions, the method could be used in parallel to a therapy against colorectal cancer, to assess markers expression with respect to normal levels, or subsequently to a therapy, to assess, in this case as well, markers expression with respect to normal levels and monitor any shift in the expression of these markers that might indicate disease recurrence.

The invention moreover provides a kit for the diagnosis of colorectal cancer from a sample of human whole blood or blood fractions comprising nucleic acids, comprising one or more aliquots of reagents for the quantitative analysis of the expression of human genes TSPAN8, LGALS4, CEACAM6, COL1A2 and optionally for a control constitutively expressed human gene. wherein said reagents can be separated for each gene or can be unified for one or more of said genes.

As mentioned above, the quantitative analysis of gene expression is based on the quantification of the mRNA of the genes of interest.

According to the invention, the human gene TSPAN8 is gene Tetraspanin 8, whose RNA has RNA Genbank accession number NM_004616.

According to the invention, the human gene COL1A2 is Collagen, type I, alpha 2 gene, whose RNA has RNA Genbank accession number NM_000089.

According to the invention, the human gene LGALS4 is Lectin, galactoside-binding, soluble, 4 gene, whose RNA has RNA Genbank accession number NM_006149.

According to the invention, the human gene CEACAM6 is Carcinoembryonic antigen-related adhesion molecule 6 gene, whose RNA has RNA Genbank accession number NM_002483. According to the invention, the sample for the kit of the present invention may be a sample of whole blood or of any one blood fraction comprising nucleic acids, like e.g. serum and/or plasma.

The reagents for the quantitative analysis for the purposes of the present invention are those commonly used by the technician in the field for nucleic acid quantitative analysis methodologies, such as, e.g., without limiting the invention thereto, real-time quantitative PCR, or digital-PCR, or ultra deep-sequencing.

The reagents specific for the analysis of each mRNA of interest could be provided in one or more aliquots distinct for each mRNA of interest or could be provided in one or more aliquots containing reagents for the quantification of one or more mRNA of interest.

According to one embodiment of the invention, the reagents for the quantitative analysis of the expression of the above-mentioned genes are Real Time PCR primers selectively specific for each of said genes.

The sequence of the mRNAs of the genes of interest being known, the technician in the field could design with extreme ease Real Time PCR primers which enable a selective quantification of the mRNAs of interest. Such primers may also be obtained from commercial sources specialized in the preparation of reagents for Real Time PCR.

According to one exemplary and non-limiting embodiment of the present invention, said primers are the primers of SEQ ID NOS: 1 and 2 for TSPAN8; the primers of SEQ ID NOS: 3 and 4 for COL1A2, the primers of SEQ ID NOS: 5 and 6 for LGALS4 and the primers of SEQ ID NOS: 7 and 8 for CEACAM6.

Furthermore, the kit according to any one of the embodiments described herein could contain reagents for quantifying the expression of one or more mRNAs of constitutively expressed (housekeeping) human genes, the expression values obtained could be used to normalize the expression values recorded for the above-described mRNAs of interest, i.e., the mRNAs of the human genes TSPAN8, LGALS4, CEACAM6, COL1A2.

Such reagents could be used to quantify, as already described above in connection with the method, one or more mRNAs of constitutive genes, enabling the normalization of the values measured for the mRNAs of the genes of interest according to the above-described equation:

$$\Delta Ct_{marker\ of\ interest} = CT_{marker\ of\ interest} - CT_{constitutive\ gene}$$

By way of example, in no way to be construed as limitative of the present invention, such reagents may be Real Time PCR primers for one or more constitutive human genes, such as, e.g., the B2M gene for which, e.g., the primers of SEQ ID NOS: 9 and 10 may be used. Moreover, the kit according to any one embodiment of the present invention could further comprise one or more reagents for total RNA or mRNA extraction and/or also reagents for reverse transcription of total RNA.

Furthermore, the kit according to any one embodiment of the invention could further comprise one or more aliquots of Total RNA or mRNA or cDNA of healthy individuals as negative controls and/or of individuals affected by colorectal cancer as positive controls.

EXAMPLES

The following examples aim at illustrating the invention without absolutely being limitative thereof.

The studies which led to the present invention were approved by the Ethics Committee of the "Sant'Orsola-Malpighi" Hospital of Bologna, Italy, and meet the requirements of the Helsinki Declaration of Ethical Principles for medical research involving human subjects.

All subjects involved signed an informed consent form before the start of the studies.

Peripheral blood samples were obtained from 67 healthy donors and 56 non-correlated patients with histological analysis confirming CRC at any stage, prior to surgical therapy and without addition of chemical or radiological treatments to the surgical therapy.

To reduce the risk of sample contamination from needle-carried epithelial cells, the first ml of blood was discarded.

RNA Extraction

Whole blood, put in a tube containing EDTA, was treated for lysis within one hour from collection, by adding the reagent TRIzol LS (Invitrogen, Carlsbad, Calif., USA) and total RNA was extracted according to the provider's protocol. Total RNA extracted from 1 ml of blood was subjected to precipitation with standard ethanol, and the pellet was dissolved in 15 μl of RNAse-free water at a final concentration of up to 0.5 μg/μl and stored at −20° C.

The concentration of all samples of total RNA was quantified with a Nanodrop ND-2000 spectrophotometer (Thermo Fisher Scientific, Waltham, Mass.).

qRT-PCR 300 ng of RNA were subjected to reverse transcriptase with the RevertAid First Strand cDNA Synthesis kit (Carlo Erba Reagents, Milan, Italy) and amplified by using the EvaGreen system (Bio-Rad, Hercules, Calif., USA), according to the provider's instruction. The list of the primers used for the candidate markers and the reference genes is reported in Table 2 below (SIGMA ALDRICH, Milan, Italy).

The Real-time PCR reactions were carried out with the CFX96 instrument (Bio-Rad, Hercules, Calif.), in duplicate, at 95° C. for 10 min, followed by 40 cycles at 95° C. for 15 sec and 60° C. for 1 min, with melting curve analysis. Each qPCR run always included a negative control without cDNA, and a positive control of cDNA derived from cell line HT-29, in which it is known that the genes of interest are present. The reaction efficiency (E) was calculated from the slope of the standard curve generated with 10-fold serial dilutions of the calibration cDNA according to the formula:

$$E = [10(-1/\text{slope}) - 1] \times 100.$$

Statistical Analysis

Student's test was adopted to compare the expression levels analysed between the CRC cases and the controls. ROC (Receiving Operating Characteristic) curve analysis was used to assess the accuracy with which the parameters diagnosed CRC, for the purpose of discriminating between CRC patients and controls. Calculations both of the area above the curve and of the intervals corresponding to a 95% confidence were assessed by using Medcalc version 14 for statistical analyses. In order to determine the markers cutoff enabling the best discrimination between the two groups, the discriminating analysis was carried out by using the statistical program SPSS, version 22, as described in Wang H, Zhang X, Wang L, Zheng G, Du L, Yang Y, et al. Investigation of cell free BIRC5 mRNA as a serum diagnostic and prognostic biomarker for colorectal cancer. Journal of surgical oncology. 2014; 109(6):574-9. The sets of healthy individuals and of CRC patients were considered as a grouping variable, and the four independent markers were grouped together as foreseen variable.

TABLE 2

The preferred markers were selected on a total of 38'104 loci.

| Gene symbol | Gene name | RNA Genbank Accession No. | sequence | SEQ ID NO |
|---|---|---|---|---|
| TSPAN8 | Tetraspanin 8 | NM_004616 | gctgcatgcttctgttgtttt | 1 |
| | | | aacacaattatggcttcctg | 2 |
| EPCAM | Epithelial cell adhesion molecule | NM_002354 | gtatgagaaggctgagataaag | 11 |
| | | | cttcaaagatgtcttcgtcc | 12 |
| SPINK1 | Serine peptidase inhibitor, Kazal type 1 | NM_003122 | tgaaaatcggaaacgccagac | 13 |
| | | | gcggtgacctgatgggattt | 14 |
| COL1A2 | Collagen, type I, alpha 2 | NM_000089 | gtggttactactggattgac | 3 |
| | | | ctgccagcattgatagtttc | 4 |
| CDH1 | *Homo sapiens* cadherin 1, type 1, E-cadherin | NM_004360 | cagtacaacgacccaaccca | 15 |
| | | | cacgctgacctctaaggtgg | 16 |
| LGALS4 | Lectin, galactoside-binding, soluble, 4 | NM_006149 | ttaccctggtcccggacatt | 5 |
| | | | agcctcccgaaatatggcac | 6 |
| CEACAM6 | Carcinoembryonic antigen-related adhesion molecule 6 | NM_002483 | cacagtctctggaagtgctcc | 7 |
| | | | ggccagcactccaatcgt | 8 |
| B2M | Beta-2-microglobulin | NM_004048 | tgcctgccgtgtgaaccatgt | 9 |
| | | | tgcggcatcttcaaacctccatga | 10 |

Forward primer above, reverse primer below.

Data Set Meta-Analysis by TRAM

A systematic meta-analysis, comprehensive of the differential gene expression in CRC and normal blood, was carried out in order to identify the mRNAs with the highest expression ratio between CRC and blood in order to select the best candidates as biomarkers. By the Transcriptome Mapper TRAM, it was possible to manage experimental platforms with different numbers of genes in order to maximize the information that could be extracted from the data set. 37 GEO series were selected from CRC, with an additional 23 series for blood. The series selected included, respectively, a total of 2532 and 958 samples. For each series, a random sampling was carried out which included more than 10 samples, thereby reducing the number of analysed samples to 349 for CRC and 200 for blood (14% and 21% of the total, respectively). Analysis of the integrated and normalized final data set enabled to identify genes, among a total of 38'104 expressed loci, with an expression value available both in group 'A' (CRC) and in group 'B' (blood), with the highest absolute ratios 'A'/'B' between the expression value in the CRC tissue with respect to blood cells.

CRC Markers Selection

A further screening of the results of the TRAM database was carried out in order to identify the potentially best loci, which are summarized in Table 3 below.

Table 3. Selected candidate markers, represented by the first 15 loci with the best 'A'/'B' ratio, having over 50% of sample data for each of the two pools.

TABLE 3

| Gene name | 'A' Value colorectal cancer | 'B' Value Normal blood | 'A'/'B' ratio | Position | Data points 'A' | Data points 'B' | DS as 'A' expression % | DS as 'B' expression % |
|---|---|---|---|---|---|---|---|---|
| TSPAN8 | 2,313.03 | 13.12 | 176.36 | chr12 | 349 | 185 | 67.66 | 424.15 |
| EPCAM | 2,111.87 | 13.60 | 155.27 | chr2 | 354 | 222 | 69.86 | 82.81 |
| SPINK1 | 1,086.88 | 12.68 | 85.70 | chr5 | 368 | 215 | 99.51 | 107.87 |
| COL3A1 | 862.27 | 10.10 | 85.35 | chr2 | 1291 | 527 | 140.54 | 110.39 |
| CEACAM5 | 2,074.89 | 24.44 | 84.88 | chr19 | 572 | 315 | 132.13 | 144.57 |
| COL1A2 | 989.85 | 12.79 | 77.42 | chr7 | 767 | 549 | 115.82 | 131.00 |
| CDH1 | 825.52 | 11.87 | 69.56 | chr16 | 573 | 455 | 120.84 | 105.73 |
| LGALS4 | 1,980.67 | 29.50 | 67.15 | chr19 | 369 | 185 | 77.43 | 104.96 |
| KRT18 | 1,719.60 | 25.69 | 66.93 | chr12 | 482 | 318 | 88.43 | 111.69 |
| SLC26A3 | 800.45 | 12.31 | 65.01 | chr7 | 369 | 195 | 187.48 | 138.12 |
| REG1A | 776.24 | 12.54 | 61.91 | chr2 | 346 | 185 | 191.25 | 75.25 |
| FN1 | 664.80 | 11.22 | 59.25 | chr2 | 1588 | 902 | 144.43 | 125.93 |
| LUM | 556.84 | 9.40 | 59.22 | chr12 | 403 | 262 | 108.62 | 83.50 |
| CEACAM6 | 2,245.12 | 38.49 | 58.33 | chr19 | 583 | 274 | 65.15 | 480.79 |
| KRT20 | 731.52 | 12.58 | 58.13 | chr17 | 372 | 182 | 119.91 | 85.52 |

In order to select the best transcripts, considering that the expression value is expressed as percentage of the average value in the integrated expression profile (i.e., 1'000=ten times the average), the last loci of the list were further excluded, from SLC26A3 to KRT20, except CEACAM6, which has a high absolute expression value. Subsequently, locus CEACAMS, locus COL3A1, and locus KRT18 were excluded due to the presence of pseudogenes not enabling to design PCR primers specific for their mRNA, and to distinguish between mRNA and contamination by DNA. Then, 7 potential candidates were identified, which are those reported in Table 2 (with the exception of the constitutive gene B2M).

Quantitative Analysis of mRNA Markers in Blood

Each RNA sample (patients or healthy subjects) was assayed for quality and for expression of the candidate markers listed in Table 2 by quantitative PCR, and the value were normalized with the housekeeping gene B2M. Assayed genes exhibited a single peak in the analysis of the melting curve, and all negative controls yielded no detectable amplification values, corroborating amplification specificity.

Expression levels of normalized mRNAs indicated as Delta CT (cutoff cycle) were calculated, which were, respectively, 8.3±1.92 for TSPAN8; 11.23±1.36 for EPCAM; 11.88±2.87 for SPINK1; 9.59±2.37 for COL1A3; 9.9±0.9 for CDH1; 13.77±0.83 for LGALS4 and 12.8±1.08 for CEACAM6 in healthy subjects, and 11.8±1.7 for TSPAN8; 11.83±1.23 for EPCAM; 11.88±2.87 for SPINK1; 11.85±2.59 for COL1A3; 11.9±1.08 for CDH1; 11.42±2.42 for LGALS4 and 10.9±1.79 for CEACAM6 in patients affected by CRC.

Diagnostic Value of mRNA Markers in Blood for CRC

In order to assess diagnostic accuracy in terms of specificity and sensitivity of candidate markers, ROC curve analysis was carried out. The higher diagnostic accuracy (expressed in term of AUC, or area under the curve) was for markers TSPAN8 (0.93), LGALS4 (0.827), CEACAM6 (0.806) and COL1A2 (0.748). Graphic processing for these four markers is reported in FIG. 1.

Assessment of the Diagnostic Potential of the Different Combinations of the 4 mRNA Markers.

To assess the potential use of the candidate mRNAs selected as diagnostic panel for CRC, ROC analysis was carried out for every possible combination of the four most interesting markers. Table 4 shows how, by starting from the specificity and sensitivity values of each marker, it is absolutely impossible to foresee the results, in terms of specificity and selectivity, of the various combinations of markers. For instance, the combination of LGALS4 and CEACAM6 increased test specificity to 85%, and sensitivity to 92.5%, whereas the combination of LGALS4 with TSPAN8 decreased test specificity for both markers to 80%, whereas it increased selectivity to about 90%. Likewise, a combination of CEACAM6 with TSPAN8 decreased test sensitivity for both markers to 80%, whereas it increased specificity to about 92%. However, a combination of the three yielded a 92% sensitivity, but an 82% specificity.

Unexpectedly, the addition of a marker with 84.8% sensitivity and 76.7% specificity led to a >92% sensitivity and a 94% specificity.

Remarkably, the sole combination able to increase both parameters beyond 90% was the combination of all markers, in spite of only LGALS4 exhibiting a >90% value, and in spite of different combinations of the various markers not providing indications of a possible result such as that obtained with the combination of the 4 markers together.

Diagnostic Method.

1. 2 ml of peripheral blood were collected from patients affected from evident colorectal cancer and from healthy donors who had given their approval to collection with an informed consent.

2. Blood was lysed with Trizol LS following the producer's instructions. Preferably, lysis was carried out within 1-2 hours from collection.
3. Total RNA was extracted from the sample according to standard protocols of commercial kits.
4. Retrotranscription of 300 ng of RNA was carried out for each sample.
5. Real Time PCR reactions were carried out by using the primers reported in Table 2, for all combinations reported in Table 1, comprising primers for a housekeeping gene as control for data normalization.
6. Data analysis was carried out by normalizing the values measured for the mRNAs of the genes of interest according to the equation:

$$\Delta Ct_{marker\ of\ interest} = CT_{marker\ of\ interest} - CT_{constitutive\ gene}$$

The analysis thus carried out yielded the data reported in Table 1.

CONCLUSIONS

Hence, the diagnostic method and the diagnostic kit of the invention enable a screening on whole blood that can facilitate an early diagnosis of CRC. It should be stressed that the use of whole blood enables the detection of mRNA molecules present in CRC patients' blood of with an expression altered with respect to normal individuals. Collected blood is preferably lysed with Trizol LS within 1 hour from collection in order to avoid possible degradation of said molecules. The quantitative analysis of the sole TSPAN8 is already very useful, exhibiting a sensitivity slightly higher than 86% and a specificity of about 87%; all the same, the present invention enabled to improve both parameters to beyond 90%, providing a diagnostic method with a selectivity of about 92.5% and a sensitivity of about 94%, making the method more selective than colonoscopy itself, and almost as sensitive as the latter.

The invention claimed is:

1. A method for treatment of colorectal cancer in a human subject comprising administering treatment of the colorectal cancer to the subject, wherein said treatment is a chemical, radiological or surgical therapy, and wherein a whole blood and/or blood fraction sample obtained from the subject has been determined by quantitative analysis to have an overexpression of TSPAN8 and COL1A2 and an underexpression of LGALS4 and CEACAM6 with respect to reference values.

2. The method according to claim 1, wherein the administering treatment comprises surgical therapy.

3. The method according to claim 1, wherein said overexpression and said underexpression are assessed with respect to reference values from a control sample from one or more healthy individuals with respect to predetermined cutoffs for each of said mRNAs.

4. The method according to claim 1, wherein said quantitative analysis is performed by Real Time PCR.

5. The method according to claim 4, wherein said Real Time PCR is carried out using primers of SEQ ID NOS: 1 and 2 for TSPAN8, primers of SEQ ID NOS: 3 and 4 for COL1A2, primers of SEQ ID NOS: 5 and 6 for LGALS4, and primers of SEQ ID NOS: 7 and 8 for CEACAM6.

6. The method according to claim 5, wherein said Real Time PCR further comprises quantification of mRNA of one or more human constitutively expressed genes for normalization of results obtained.

7. The method according to claim 6, wherein said quantitative analysis comprises assessment of normalized ΔCt with respect to a human constitutively expressed gene for each marker and wherein individuals affected by colorectal cancer have $\Delta Ct$ of $\leq 11.9 \pm 1.7$ for TSPAN8; $\Delta Ct$ of $\leq 11.8 \pm 2.28$ for COL1A2; $\Delta Ct$ of $>11.42 \pm 2.42$ for LGALS4; and $\Delta Ct \geq 10.9 \pm 1.79$ for CEACAM6.

* * * * *

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: RT-PCR fwd primer for TSPAN8

<400> SEQUENCE: 1
gctgcatgct tctgttgttt t                                             21

<210> SEQ ID NO 2
<211> LENGTH: 20
<212> TYPE: DNA
<213> ORGANISM: Artificial Sequence
<220> FEATURE:
<223> OTHER INFORMATION: RT-PCR rev primer for TSPAN8

<400> SEQUENCE: 2
aacacaatta tggcttcctg                                               20

<210> SEQ ID NO 3
<211> LENGTH: 20
<212> TYPE: DNA
<213> ORGANISM: Artificial Sequence
<220> FEATURE:
<223> OTHER INFORMATION: RT-PCR fwd primer for COL1A2

<400> SEQUENCE: 3
gtggttacta ctggattgac                                               20

<210> SEQ ID NO 4
<211> LENGTH: 20
<212> TYPE: DNA
<213> ORGANISM: Artificial Sequence
<220> FEATURE:
<223> OTHER INFORMATION: RT-PCR rev primer for COL1A2

<400> SEQUENCE: 4
ctgccagcat tgatagtttc                                               20

<210> SEQ ID NO 5
<211> LENGTH: 20
<212> TYPE: DNA
<213> ORGANISM: Artificial Sequence
```

```
<220> FEATURE:
<223> OTHER INFORMATION: RT-PCR fwd primer for LGALS4

<400> SEQUENCE: 5
ttaccctggt cccggacatt                                           20

<210> SEQ ID NO 6
<211> LENGTH: 20
<212> TYPE: DNA
<213> ORGANISM: Artificial Sequence
<220> FEATURE:
<223> OTHER INFORMATION: RT-PCR rev primer for LGALS4

<400> SEQUENCE: 6
agcctcccga aatatggcac                                           20

<210> SEQ ID NO 7
<211> LENGTH: 21
<212> TYPE: DNA
<213> ORGANISM: Artificial Sequence
<220> FEATURE:
<223> OTHER INFORMATION: RT-PCR fwd primer for CEACAM6

<400> SEQUENCE: 7
cacagtctct ggaagtgctc c                                         21

<210> SEQ ID NO 8
<211> LENGTH: 18
<212> TYPE: DNA
<213> ORGANISM: Artificial Sequence
<220> FEATURE:
<223> OTHER INFORMATION: RT-PCR rev primer for CEACAM6

<400> SEQUENCE: 8
ggccagcact ccaatcgt                                             18

<210> SEQ ID NO 9
<211> LENGTH: 21
<212> TYPE: DNA
<213> ORGANISM: Artificial Sequence
<220> FEATURE:
<223> OTHER INFORMATION: RT-PCR fwd primer for B2M

<400> SEQUENCE: 9
tgcctgccgt gtgaaccatg t                                         21

<210> SEQ ID NO 10
<211> LENGTH: 24
<212> TYPE: DNA
<213> ORGANISM: Artificial Sequence
<220> FEATURE:
<223> OTHER INFORMATION: RT-PCR rev primer for B2M

<400> SEQUENCE: 10
tgcggcatct tcaaacctcc atga                                      24

<210> SEQ ID NO 11
<211> LENGTH: 22
<212> TYPE: DNA
<213> ORGANISM: Artificial Sequence
<220> FEATURE:
<223> OTHER INFORMATION: RT-PCR fwd primer for EPCAM

<400> SEQUENCE: 11
gtatgagaag gctgagataa ag                                        22
```

-continued

```
<210> SEQ ID NO 12
<211> LENGTH: 20
<212> TYPE: DNA
<213> ORGANISM: Artificial Sequence
<220> FEATURE:
<223> OTHER INFORMATION: RT-PCR rev primer for EPCAM

<400> SEQUENCE: 12
cttcaaagat gtcttcgtcc                                           20

<210> SEQ ID NO 13
<211> LENGTH: 21
<212> TYPE: DNA
<213> ORGANISM: Artificial Sequence
<220> FEATURE:
<223> OTHER INFORMATION: RT-PCR fwd primer for SPINK1

<400> SEQUENCE: 13
tgaaaatcgg aaacgccaga c                                         21

<210> SEQ ID NO 14
<211> LENGTH: 20
<212> TYPE: DNA
<213> ORGANISM: Artificial Sequence
<220> FEATURE:
<223> OTHER INFORMATION: RT-PCR rev primer for SPINK1

<400> SEQUENCE: 14
gcggtgacct gatgggattt                                           20

<210> SEQ ID NO 15
<211> LENGTH: 20
<212> TYPE: DNA
<213> ORGANISM: Artificial Sequence
<220> FEATURE:
<223> OTHER INFORMATION: pRT-PCR fwd primer for CDH1

<400> SEQUENCE: 15
cagtacaacg acccaaccca                                           20

<210> SEQ ID NO 16
<211> LENGTH: 20
<212> TYPE: DNA
<213> ORGANISM: Artificial Sequence
<220> FEATURE:
<223> OTHER INFORMATION: RT-PCR rev primer for CDH1

<400> SEQUENCE: 16
cacgctgacc tctaaggtgg                                           20
```